(12) United States Patent
Matsubara et al.

(10) Patent No.: US 9,669,234 B2
(45) Date of Patent: Jun. 6, 2017

(54) LIGHT-BEAM THERAPEUTIC APPARATUS

(71) Applicant: ATOM MEDICAL CORPORATION, Tokyo (JP)

(72) Inventors: Kazuo Matsubara, Tokyo (JP); Terumi Matsubara, Saitama (JP); Naoki Honma, Saitama (JP); Hiroki Suma, Saitama (JP); Yoshiyuki Tashiro, Saitama (JP)

(73) Assignee: ATOM MEDICAL CORPORATION, Tokyo (JP)

( * ) Notice: Subject to any disclaimer, the term of this patent is extended or adjusted under 35 U.S.C. 154(b) by 669 days.

(21) Appl. No.: 13/834,171

(22) Filed: Mar. 15, 2013

(65) Prior Publication Data
US 2014/0012354 A1   Jan. 9, 2014

(30) Foreign Application Priority Data
Jul. 9, 2012 (JP) ................................ 2012-153432

(51) Int. Cl.
*A61N 5/06* (2006.01)
*F21V 8/00* (2006.01)

(52) U.S. Cl.
CPC ......... *A61N 5/0621* (2013.01); *G02B 6/0006* (2013.01); *A61N 2005/0664* (2013.01)

(58) Field of Classification Search
CPC .................................................. A61N 5/0621
USPC .............................. 607/88, 90, 93
See application file for complete search history.

(56) References Cited

U.S. PATENT DOCUMENTS

| 6,004,045 A * | 12/1999 | Snackers et al. ............... 385/92 |
| 6,554,495 B1 * | 4/2003 | Zhu et al. ........................ 385/92 |
| 6,719,447 B1 * | 4/2004 | Woodward et al. .......... 362/573 |
| 2002/0138120 A1 * | 9/2002 | Whitehurst ..................... 607/88 |
| 2009/0030490 A1 * | 1/2009 | Pipe et al. ...................... 607/91 |

FOREIGN PATENT DOCUMENTS

| JP | 2005-056608 | 3/2005 |
| JP | 2006-217990 | 8/2006 |
| JP | 2006-223665 | 8/2006 |

* cited by examiner

*Primary Examiner* — William Thomson
*Assistant Examiner* — Sebastian X Lukjan
(74) *Attorney, Agent, or Firm* — Wenderoth, Lind & Ponack, L.L.P.

(57) ABSTRACT

A light-beam therapeutic apparatus for ensuring patient safety. The light-beam therapeutic apparatus includes an apparatus body portion having a light source; a light guide rod that guides light from the light source, a connecting socket, a cooling fan, an electronic component that performs control required for a therapy, and a control display panel that displays contents of the therapy; a therapeutic portion including a light guide portion including a plurality of bundled optical fibers, and a pad portion formed of the optical fibers spread out adjacently to one another into a flat-panel shape. The therapeutic portion is formed into a light-receiving plug that is insertable into a connecting socket of the apparatus body portion. The light-receiving plug is configured to be kept in a coupled state by an attracting action of a permanent magnet provided on a side of the connecting socket.

9 Claims, 4 Drawing Sheets

LIGHT-BEAM THERAPEUTIC APPARATUS

BACKGROUND OF THE INVENTION

1. Field of the Invention

The present invention relates to a therapeutic apparatus used mainly for a therapy for hyperbilirubinemia of neonatal infants and, to a light-beam therapeutic apparatus superior in safety including an apparatus body portion as a light source having an operating section and a display unit and, separately from the apparatus body portion, an optical fiber connected to the light source and a pad portion configured to place a neonatal infant thereon for performing a therapy.

2. Prior Art

A plurality of medical light-beam therapeutic apparatuses of this type configured to perform a therapy by guiding a light beam from a light source to a therapeutic portion via an optical fiber as described below, although not a pad-type, are known.

As a first known technology, there is proposed a light irradiating apparatus or a light-beam therapeutic apparatus including an apparatus body portion having a light source, a light guide portion extending from the apparatus body portion, and a hand piece coupled to the light guide portion on the side opposite from the apparatus body portion, and being configured to irradiate an object to be irradiated with light from the hand piece, characterized in that the light guide portion is composed of an optical fiber bundle having bundled optical fibers, and a light-homogenizing member configured to substantially homogenize an output distribution of light irradiated from the optical fiber bundles is disposed in the interior of the hand piece portion (see JP-A-2005-56608).

In the light-beam therapeutic apparatus of the first known technology, since the therapy is achieved by irradiating affected areas of human bodies or animals with a substantially homogenized output light, therapeutic effects desirable for a medical application which requires a homogenous output light distribution such as a thermal therapy for joint pain or bedsore by means of infrared ray, treatment of macula by means of laser beams may be expected. In particular, this apparatus is effective when treating tissues of cancer or the like by a photodynamic therapy (PDT) because light irradiation with high homogeneity is possible. In addition, since the irradiation is achieved from many angles freely by the optical fiber bundle, the operability is superior.

A second known technology is a light-beam therapeutic apparatus including a light source, a plurality of first optical fibers optically connectable with the light source, a plurality of probes optically connected to the plurality of first optical fibers respectively, and a light guide controller configured to switch the first optical fiber to be optically connected to the light source from among the plurality of first optical fibers (see JP-A-2006-223665).

In the light-beam therapeutic apparatus of the second known technology, it is possible to irradiate an affected area with a light-beam output from the light source from each of the plurality of probes without attenuating the output. Therefore, a therapy for a deep portion of a body is facilitated and reduction of therapeutic time is achieved. In addition, since irradiation from the plurality of probes is achieved using a single light source, relatively low production costs are achieved in comparison with the light-beam therapeutic apparatus of the prior art that requires the same number of light sources (for example, laser elements) as the probes.

A third known technology is a light-beam therapeutic apparatus including an optical system configured to converge and guide light from a plurality of different light sources, an optical fiber cable configured to multiply carry the converged and guided light, and a hand piece including at least one projector lens configured to project an output light from a distal end of the optical fiber cable disposed therein (see JP-A-2006-217990).

In the light-beam therapeutic apparatus of the third known technology, the plurality of light sources are provided intensively into one machine and hence space saving is achieved. Light in a plurality of different wavelength regions may be combined as needed.

In the light-beam therapeutic apparatus of the first known technology, the light guide portion is composed of the optical fiber bundle including bundled optical fibers, a light-homogenizing member configured to substantially homogenize the output distribution of the light irradiated from the optical fiber bundle is installed in the interior of the hand piece portion, so as to perform a therapy by irradiating the visible affected area with homogenous and spot-like output light. However, the light-homogenizing member and the optical fiber bundle are fixedly and continuously coupled instead of coupling by insertion of a plug into a socket so as to prevent the light emitted from the light source from leaking to the outside, whereby the light source and the optical fiber bundle are prevented from being easily separable.

The light-beam therapeutic apparatus according to the second known technology is configured to be capable of irradiating the affected portion in the body with the light-beam output from the single light source from each of the plurality of optical fibers and probes provided at distal ends thereof without attenuating the output on the basis of time division by the light guide controller. However, the light-source side and the optical-fiber side are fixedly and continuously coupled to the light guide controller disposed between the light source and the optical fiber so as not to be easily separable.

In order to achieve the space saving, the light irradiating apparatus of the third known technology is configured to include the plurality of different light sources provided intensively into a single machine (housing), a single multiple-carrying optical fiber cable configured to optically converge and guide light from these light sources so as to extend from an upper surface of the single machine (housing), and a lens configured to project the combined light in the plurality of different wavelength regions from the distal end of the optical fiber cable and irradiate the affected area with the combined light. However, in the same manner as the first and second known technologies, the machine including the light source integrated therein and the optical fiber cables are fixedly and continuously coupled so as not to be easily separable.

For the light-beam therapeutic apparatus of this type except for those of compact and portable types, a specific therapy room is provided and operators such as the doctor or nurse who handle the therapeutic apparatus perform a therapy by operating the apparatus using a remote controller from a space partitioned so as not to be exposed to therapeutic light beams. The compact and portable light-beam therapeutic apparatus for neonatal infants is used by being placed on a cradle with wheels attached and brought into a neonatal infants' room isolated from the outside in many cases. In the neonatal infants' room, a number of beds for neonatal infants are arranged and, especially, a light-beam therapeutic apparatus which emits blue, green, or blue-green light for perform a therapy for hyperbilirubinemia is used in such a manner that a neonatal infant accommodating space is provided on part of the cradle, and a therapy is performed in a state in which the neonatal infant is accommodated in the space. However, the doctor or the nurse who handles the therapeutic apparatus operates with specific eyeglasses because looking at light beams of the blue, green, or blue-green light for a long time negatively affects his or her eyes.

However, in the portable therapeutic apparatus of this type, there are a connection of a power source cord with respect to the apparatus body and a connection of the light-guide optical fibers with respect to the light source in the apparatus body, and parts of the cord or the optical fibers protrude from the cradle. However, in the operation of moving the neonatal infant or changing the body position for the therapy, there is a case where the cradle or the apparatus body portion falls, especially, in a case where the optical fibers are pulled or the operator's hand or elbow is unintentionally caught by the protruded portion and hence the operator lifts up and moves the neonatal infant abruptly and strongly in a mad rush, such that the delicate skin may be injured or the therapeutic apparatus may be dropped to the floor and hence broken. Therefore, there is a safety problem.

SUMMARY OF THE INVENTION

Accordingly, it is an object of the invention to provide a compact and portable light-beam therapeutic apparatus which prevents a cradle or an apparatus body portion from falling even though the optical fibers are pulled or an operators hand or elbow is unintentionally caught by a protruded portion and hence prevents frantic handling of neonatal infants and prevents occurrence of the breakage of the therapeutic apparatus thereby.

In order to solve the above described problem, there is provided a light-beam therapeutic apparatus comprising: an apparatus body portion including at least a light source, a light guide rod configured to guide light from the light source, a connecting socket to which an end portion of the light guide rod faces, a cooling fan configured to cool the light source, an electronic component configured to perform control required for a therapy, and a control display panel configured to display the contents of therapy set by operating the electronic component; and a therapeutic portion including a light guide portion having a plurality of bundled optical fibers, and a pad portion formed of the optical fibers spread out adjacently to one another into a flat-panel shape, wherein an end portion of the light guide portion of the therapeutic portion is formed into a light-receiving plug insertable into the connecting socket of the apparatus body portion, and the light-receiving plug is configured to be kept in a coupled state by an attracting action of a permanent magnet provided on a side of the connecting socket.

Preferably, the light-beam therapeutic apparatus further includes a sensor configured to detect whether or not the light-receiving plug is inserted on the connecting socket side, and the sensor has a function to turn a light source ON only when the light-receiving plug is inserted into the connecting socket.

Preferably, the sensor is either an optical sensor or a mechanical sensor, and preferably, the light-beam therapeutic apparatus further includes a sliding-type shutter provided adjacently to the connecting socket of the apparatus body portion and urged in the direction of covering the connecting socket.

According to the light-beam therapeutic apparatus of the invention, even if the elbow or the like of operators such as the doctor or nurse is erroneously or unintentionally caught by the pad portion and hence the pad portion is pulled, the light-receiving plug immediately comes off the connecting socket and the light source is turned OFF to prevent the apparatus body portion from falling or dropping and, furthermore, the blue, green, or blue-green light is not irradiated to the outside from the opening of the connecting socket. Therefore, the neonatal infant or the operator is prevented from being directly exposed to the blue, green, or blue-green light beams, so that the superior safety is ensured.

According to the light-beam therapeutic apparatus of the invention, a sliding-type shutter provided adjacently to the connecting socket of the apparatus body portion and urged in the direction of covering the connecting socket is provided, so that an effect in which the blue, green, or blue-green light is prevented from being irradiated to the outside, is advantageously achieved.

DETAILED DESCRIPTION OF THE PREFERRED EMBODIMENTS

Figure 1:
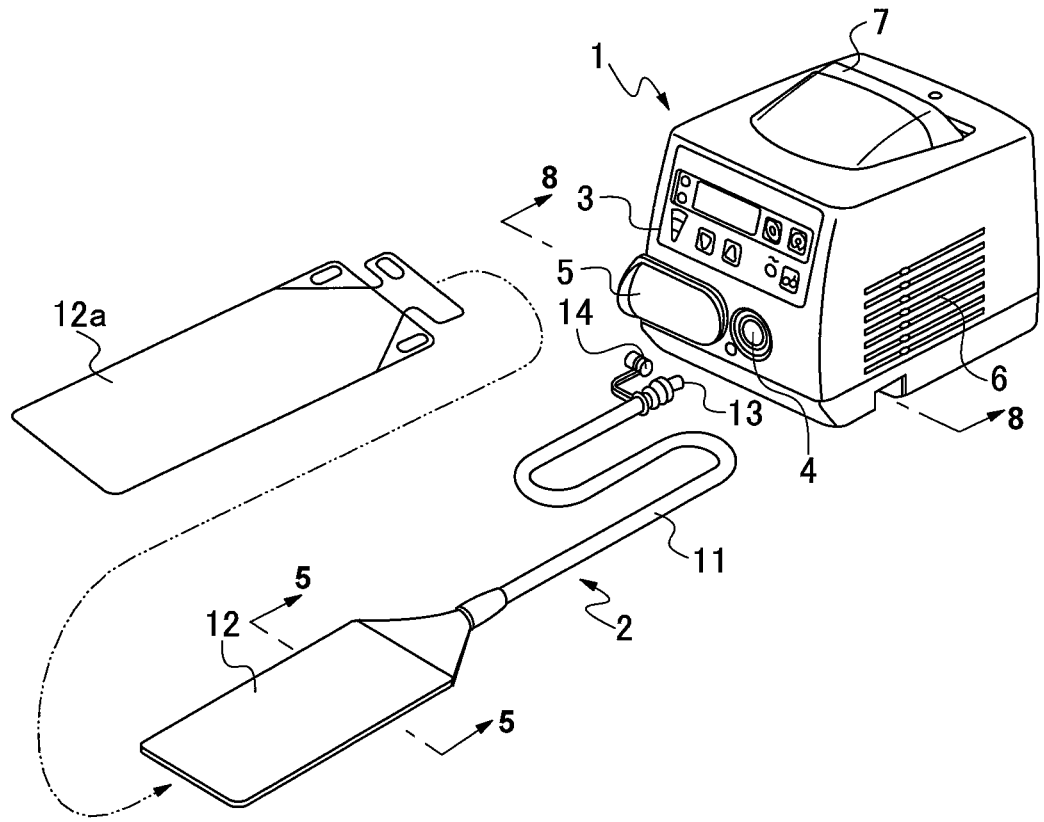
FIG. 1 is a perspective front view of a light-beam therapeutic apparatus according to an embodiment of the invention illustrating a state in which an apparatus body portion and a therapeutic portion are separated.
Figure 2:
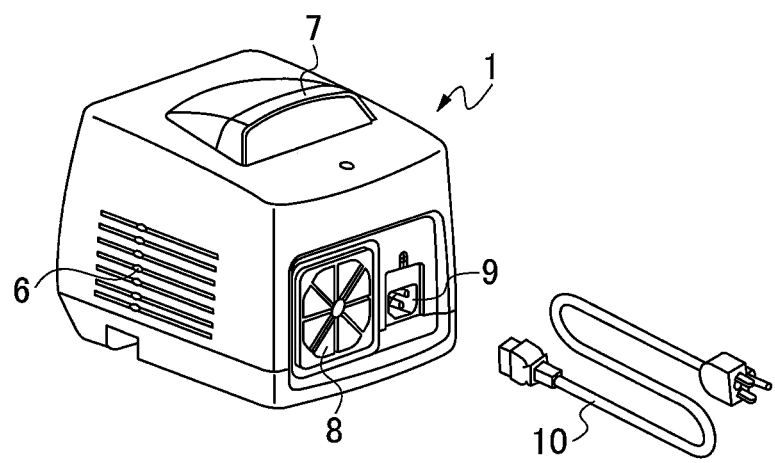
FIG. 2 is a perspective back view of the same light-beam therapeutic apparatus illustrating a state in which the apparatus body portion and a power source cord are separated.

Referring now to the drawings, the light-beam therapeutic apparatus according to an embodiment of the invention will be described. In FIGS. 1 and 2, a light-beam therapeutic apparatus according to the invention includes an apparatus body portion 1 and a therapeutic portion 2 configured to be connectable and disconnectable with respect to the apparatus body portion 1.

The apparatus body portion 1 includes a control display panel 3 as an operating section provided on the front side, a connecting socket 4 of the therapeutic portion 2, and a sliding-type shutter 5 configured to open and close the connecting socket 4 and be urged by springs, a ventilating opening 6 provided on both side surfaces and a bottom portion thereof, and a grip portion 7 provided on an upper surface thereof. In addition, on the back side, a filter 8 for air supplied by a cooling fan and a power source socket 9 are provided, and a suitable power source cord 10 is connected to the power source socket 9.

The therapeutic portion 2 includes a light guide portion 11 including a plurality of flexile optical fibers bundled into a rod shape, and a pad portion 12 formed by placing the optical fibers from the light guide portion 11 into a flat shape in proper alignment in a spread manner to allow a neonatal infant to be placed thereon and configured to emit light substantially homogenously as a whole. A free end side of the light guide portion 11 is formed into a shape of a light-receiving plug 13, and in the vicinity of the light-receiving plug 13, a suitable cap 14 is provided so as to cover the light-receiving plug 13 for protecting the optical fibers.

Figures 3, 4, 5:
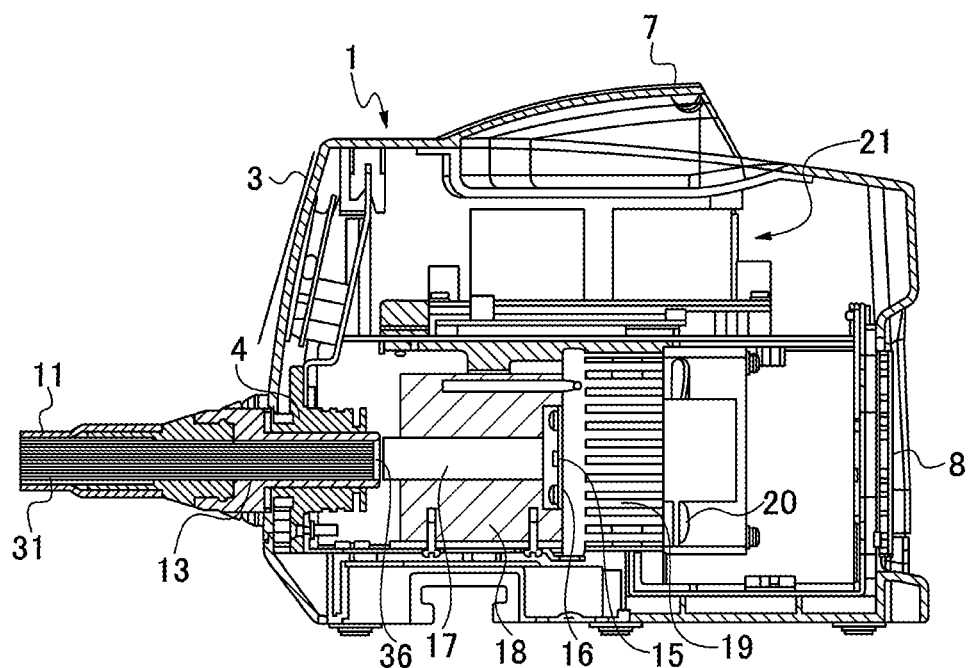
FIG. 3 is a partly omitted vertical cross-sectional view of the same light-beam therapeutic apparatus illustrating a state in which the apparatus body portion and the therapeutic portion are connected.
FIG. 4 is a front view of the same light-beam therapeutic apparatus illustrating a control display panel.
FIG. 5 is an enlarged cross-sectional view taken along the line 5-5 in FIG. 1.

The apparatus body portion 1 includes, as illustrated in FIG. 3, a substrate 16 on which a light source 15 composed of blue, green, or blue-green LEDs, for example, is mounted in the interior thereof, and a light guide rod 17 of core clad specifications configured to guide light so as to prevent the beams from being scattered is disposed on the light-emitting side of the light source 15, that is, on the front side via a mounting member 18, and a distal end portion of the light guide rod 17 opposes the connecting socket 4. The substrate 16 is mounted in tight contact with a heat radiating member 19 for radiating heat of the light source 15, a cooling fan 20 for supplying air for cooling and thermal radiation is disposed on the back side of the heat radiating member 19, and, in addition, a plurality of electronic components 21 required for controlling the function of the apparatus body portion 1 is mounted thereon.

As illustrated in FIG. 4, the control display panel 3 includes a lamp (light source) time display lamp 22, a patient irradiation time display lamp 23, a light adjustment display portion 24 for displaying high, medium, and low, a light-adjustment button 25, a display unit 26 for displaying irradiation time or messages, a lamp button 27, a patient button 28, a pilot lamp 29, and a power source switch 30, and is configured to allow the operation of the function controlling the electronic components 21 described above and setting the function of the apparatus body portion 1 to a therapeutic state suitable for the patient, and allow any medical staff to visually confirm the therapeutic state of the patient at any time from the control display panel 3.

As illustrated in FIG. 5, the pad portion 12 of the therapeutic portion 2 is formed by placing a plurality of optical fibers 31 (for example, PJR-FB500 manufactured by TORAY INDUSTRIES, INC.) connected from the light guide portion 11 in proper alignment flatly and adjacently to one another, adhering the optical fibers 31 placed in adjacent alignment to one another on a flexible sheet-shaped highly-reflective member 33 (for example, RAY BRIGHT RB97UN-BM manufactured by ATT) using an adhesive device 32, for example, a double-faced adhesive tape (for example, a double-faced tape 1510 for skin manufactured by 3M), and fixedly securing the same in a stable state. Subsequently, the exposing processing is applied to the upper surfaces of the optical fibers 31 secured in the aligned manner and the entire part is covered with the bag-shaped cover member 34 formed of a translucent flexible sheet member. In this case, the pad portion 12 is formed by using a bag-shaped cover member 34 formed with two flat upper and lower layers of bag members 34a and 34b partitioned by a non-yellowing highly-transparent and highly-flexible urethane sheet as the translucent flexible sheet member, filling the bag member 34a on the upper side with high-molecular gel such as non-yellowing transparent and flexible urethane gel or styrene gel to form a protecting surface layer portion 35, and inserting and storing the optical fibers 31 fixedly secured to the highly-reflective member 33 and subjected to the exposing processing in the bag member 34b on the lower side. Furthermore, when in use, the pad portion 12 is covered with a pad cover 12a formed of a highly flexible nonwoven fabric having water absorbing properties and ecological compatibility and formed into a bag shape having the same shape as the pad portion 12.

When using the therapeutic apparatus, the apparatus body portion 1 and the therapeutic portion 2 are configured to be connected to each other by inserting the light-receiving plug 13 of the therapeutic portion 2 into the connecting socket 4 of the apparatus body portion 1 as illustrated in FIG. 3, whereby an optical path formed in the light guide portion 11 including the light source 15, the light guide rod 17, and the plug 13 by the optical fibers 31 is established, so that preset light is irradiated from the pad portion 12. However, heat is generated by the light emission of the LEDs of the light source 15. The LEDs by themselves are maintained at a junction allowable temperature (125° C.) or below via the heat-radiating member 19 by air supplied positively by the cooling fan 20. Therefore, the light guide rod 17 located on the irradiating side is irradiated with a high-temperature light equal to or higher than the junction allowable temperature, so that the optical fibers 31 in the light-receiving plug 13 opposing the light guide rod 17 may be melted by high-temperature light and lose a light guiding function.

Therefore, in order to prevent such a situation, a translucent thermal insulation member 36 such as heat resistant glass is disposed between the light guide rod 17 and the light-receiving plug 13 preferably at an end portion of the light-receiving plug 13 according to convenience of maintenance. The thickness of the thermal insulation member 36 such as the heat resistant glass is selected from a range on the order of 1 to 3 mm so as not to impair the light guide function. In other words, the thermal insulation member 36 is necessarily disposed in the optical path between the light source 15 and the pad portion 12.

Referring now to FIG. 6 to FIG. 9, maintenance and safety of connection between the apparatus body portion 1 and the therapeutic portion 2 of the invention will be described.

Figure 6:
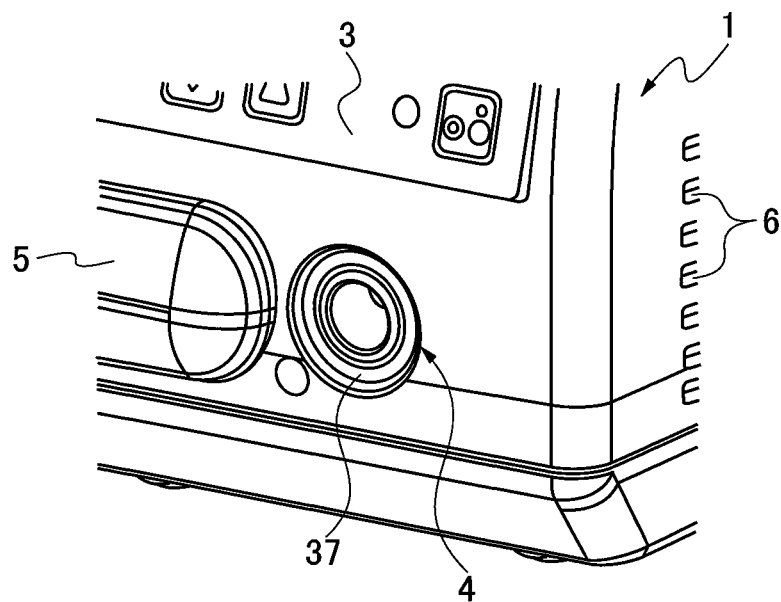
FIG. 6 is a perspective view illustrating a socket portion of the apparatus body portion of the same light-beam therapeutic apparatus in an enlarged view.
Figure 7:
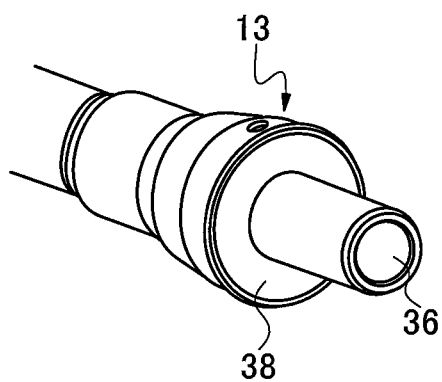
FIG. 7 is a perspective view illustrating a plug portion of the therapeutic portion of the same light-beam therapeutic apparatus in an enlarged view.

As illustrated in FIG. 6 and FIG. 7, a ring-shaped permanent magnet 37 is disposed at an opening of the connecting socket 4 of the apparatus body portion 1 and a ring-shaped magnetic force receiving plate, that is, a metallic plate 38 is disposed on a surface of the light-receiving plug 13 on the therapeutic portion 2 side coming into abutment with the connecting socket 4. In this manner, with the provision of the permanent magnet 37 and the metallic plate 38, the light-receiving plug 13 of the therapeutic portion 2 is inserted into and connected to the connecting socket 4 of the apparatus body portion 1. However, the connection is not maintained by a frictional force generated by the insertion of the plug 13 into the socket 4, but the connection of the light-receiving plug 13 is maintained by an attracting force of the permanent magnet 37 on the connecting socket 4 side.

In this case, if the permanent magnet 37 and the metallic plate 38 are brought into tight contact with each other, the permanent magnet 37 and the metallic plate 38 cannot be separated unless a relatively strong force is applied. Therefore, both members are set to oppose each other at a distance that does not come into tight contact with each other, for example, at a distance on the order of 0.5 to 1 mm. With the distance of this extent, the attracting force of the permanent magnet 37 acts on the metallic plate 38 even in a state in which the permanent magnet 37 and the metallic plate 38 are not in tight contact with each other, so that the connection of the light-receiving plug 13 inserted into the connecting socket 4 is stably maintained. In addition, since the light-receiving plug 13 comes off easily when a pulling action is unintentionally applied to the therapeutic portion 2, the cradle on which the apparatus body portion 1 is placed is prevented from falling or the apparatus body portion 1 is prevented from dropping therefrom and being broken.

Figure 8:
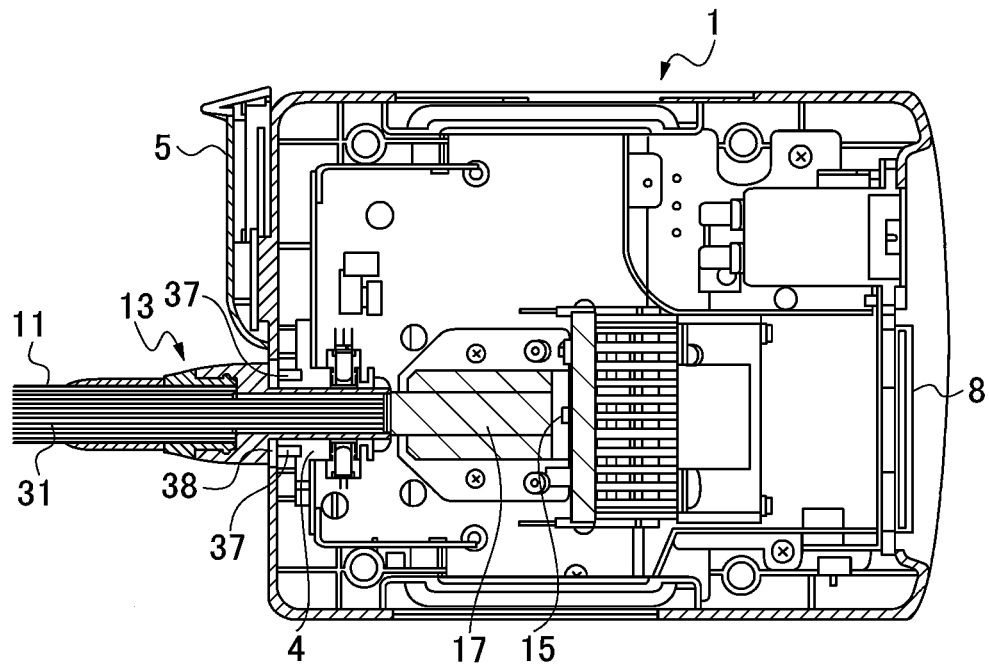
FIG. 8 is an enlarged cross-sectional view taken along the line 8-8 in FIG. 1.
Figure 9:
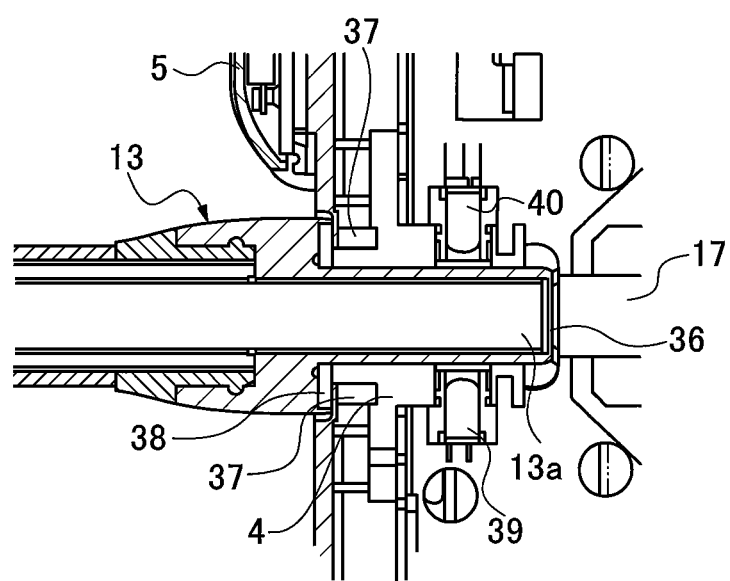
FIG. 9 is a cross-sectional view illustrating a connecting portion between the apparatus body portion and the therapeutic portion of the same light-beam therapeutic apparatus.

In addition, as illustrated in FIG. 8 and FIG. 9, for example, a sensor configured to detect whether or not the therapeutic portion 2 is connected to the apparatus body portion 1 is provided. This sensor is essentially a sensor to detect whether or not the light-receiving plug 13 is inserted into the connecting socket 4, and is an optical sensor including a light-emitting element and a light-receiving element, for example. The optical sensor includes a light-emitting diode 39 and a photodiode 40 disposed on both sides of the connecting socket 4 so as to oppose each other, light from the light-emitting diode 39 is interrupted when an insertion portion 13a of the light-receiving plug 13 is inserted into the connecting socket 4, the light source 15 including LEDs is turned ON by a signal from the photodiode 40 to irradiate with blue, green, or blue-green light, whereby the blue, green, or blue-green light is irradiated from the pad portion 12 via the optical fibers 31 in the light guide portion 11 and a therapy is achieved. The sensor may be of a type in which a mechanical switch is turned ON when the light-receiving plug 13 is inserted. Also, the arrangement of the light-emitting diode 39 and the photodiode 40 is preferably horizontal in order to protect the connecting socket 4 from incoming dust or motes.

When the light-receiving plug 13 comes apart from the connecting socket 4 if the therapeutic portion 2 is pulled unintentionally during the therapy for example, the light source 15 is immediately turned OFF and irradiation of the blue, green, or blue-green light is stopped and, simultaneously, the sliding-type shutter 5 automatically covers the opening of the connecting socket 4 to prevent the blue, green, or blue-green light from being irradiated outside, so that the neonatal infant and the operator are prevented from being exposed directly to the blue, green, or blue-green light. Suppose there is a trouble in the sensor, the external radiation of the blue, green, or blue-green light may be interrupted by the presence of the sliding-type shutter 5. Essentially, double safety is secured by the maintenance of connection by the above-described permanent magnet, and the sensor configured to detect whether or not the therapeutic portion 2 is connected to the apparatus body portion 1.

In this manner, the light-beam therapeutic apparatus includes the apparatus body portion 1 provided at least with the light source 15, the electronic components 21 having a control function, and the control display panel 3 configured to allow the setting of control and display the set contents, and the therapeutic portion 2 connected to the apparatus body portion 1 via the light guide portion 11 having the optical fibers 31 in the interior thereof and configured to irradiate the blue, green, or blue-green light from the pad portion 12 to perform a therapy for the neonatal infant; is configured to be activated by laying down a neonatal infant on the light-emitting surface of the pad portion 12 on his or her back and operating the control display panel 3 of the apparatus body portion 1 for setting the apparatus for the therapy, so that an efficient therapy for the skin of the neonatal infant in contact with the pad portion 12 is achieved. Incidentally, in order to secure the safety in the usage of the light-beam therapeutic apparatus, the light-receiving plug 13 of the therapeutic portion 2 inserted into and connected to the connecting socket 4 of the apparatus body portion 1 is configured to be kept in the coupled state by the attracting action of the permanent magnet 37 provided on the connecting socket 4 side, the sensor for detecting whether or not the light-receiving plug 13 is inserted is provided on the connecting socket 4 side, and the sensor is configured to have a function to turn the light source 15 ON only when the light-receiving plug 13 is inserted into the connecting socket 4. Accordingly, even if the elbow or the like of the operator such as the doctor or nurse is erroneously or unintentionally caught by the pad portion 12 and hence the pad portion 12 is pulled, the light-receiving plug 13 immediately comes off the connecting socket 4 and the light source 15 is turned OFF to prevent the apparatus body portion 1 from falling or dropping and, furthermore, the blue, green, or blue-green light is not irradiated to the outside from the opening of the connecting socket 4. Therefore, the neonatal infant or the operator is prevented from being directly exposed to the blue, green, or blue-green light beams, so that superior safety is ensured.

The light-beam therapeutic apparatus of the embodiment is enhanced in safety by being configured to avoid breakage due to the falling or dropping of the compact and portable light-beam therapeutic apparatus, and prevent the blue, green, or blue-green light from being irradiated to the outside from the opening of the connecting socket, and hence is apreferable as the light-beam therapeutic apparatus of this type.

What is claimed is:

1. A light-beam therapeutic apparatus comprising:
an apparatus body portion including a light source, a light guide rod configured to guide light from the light source, a connecting socket facing an end portion of the light guide rod, a cooling fan configured to cool the light source, an electronic component configured to perform control required for a therapy, and a control display panel configured to display contents of the therapy set by operating the electronic component;
a therapeutic portion including a light guide portion having a plurality of bundled optical fibers, the optical fibers being spread out adjacently to one another into a flat-panel shape so as to define a pad portion, wherein an end portion of the light guide portion of the therapeutic portion is formed into a light-receiving plug that is insertable into the connecting socket of the apparatus body portion; and
a translucent thermal insulation member disposed between the light guide rod and the light-receiving plug,
wherein the light-receiving plug is configured to be kept in a coupled state by an attracting action of a permanent magnet provided on a side of the connecting socket.

2. The light-beam therapeutic apparatus according to claim 1, further comprising:
a sensor configured to detect whether or not the light-receiving plug is inserted into the connecting socket, wherein
the sensor has a function to turn the light source ON only when the light-receiving plug is inserted into the connecting socket.

3. The light-beam therapeutic apparatus according to claim 2, wherein the sensor is either an optical sensor or a mechanical sensor.

4. The light-beam therapeutic apparatus according to claim 1, further comprising a sliding-type shutter provided adjacently to the connecting socket of the apparatus body portion and urged in the direction of covering the connecting socket.

5. The light-beam therapeutic apparatus according to claim 2, further comprising a sliding-type shutter provided adjacently to the connecting socket of the apparatus body portion and urged in the direction of covering the connecting socket.

6. The light-beam therapeutic apparatus according to claim 3, further comprising a sliding-type shutter provided adjacently to the connecting socket of the apparatus body portion and urged in the direction of covering the connecting socket.

7. The light-beam therapeutic apparatus according to claim 1, wherein the translucent thermal insulation member is disposed at an end portion of the light-receiving plug.

8. The light-beam therapeutic apparatus according to claim 7, wherein the translucent thermal insulation member comprises heat resistant glass.

9. The light-beam therapeutic apparatus according to claim 1, wherein the translucent thermal insulation member comprises heat resistant glass.

* * * * *